US008620040B2

(12) United States Patent
Grosskopf

(10) Patent No.: US 8,620,040 B2
(45) Date of Patent: Dec. 31, 2013

(54) METHOD FOR DETERMINING A 2D CONTOUR OF A VESSEL STRUCTURE IMAGED IN 3D IMAGE DATA

(75) Inventor: Stefan Grosskopf, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 1028 days.

(21) Appl. No.: 12/648,330

(22) Filed: Dec. 29, 2009

(65) Prior Publication Data

US 2010/0166283 A1 Jul. 1, 2010

(30) Foreign Application Priority Data

Dec. 30, 2008 (DE) .......................... 10 2008 063 326
Jan. 29, 2009 (DE) .......................... 10 2009 006 636

(51) Int. Cl.
 *G06K 9/00* (2006.01)
(52) U.S. Cl.
 USPC ......................................................... 382/128
(58) Field of Classification Search
 USPC ................................................. 382/128–133
 See application file for complete search history.

(56) References Cited

U.S. PATENT DOCUMENTS

| 5,999,587 | A * | 12/1999 | Ning et al. ........................ 378/4 |
| 6,201,543 | B1 * | 3/2001 | O'Donnell et al. ............ 345/420 |
| 6,643,533 | B2 | 11/2003 | Knoplioch et al. |
| 6,728,566 | B1 * | 4/2004 | Subramanyan et al. ...... 600/407 |
| 6,782,284 | B1 | 8/2004 | Subramanyan et al. |
| 6,842,638 | B1 * | 1/2005 | Suri et al. ...................... 600/425 |

(Continued)

FOREIGN PATENT DOCUMENTS

DE 102007019554 A1 11/2008
DE 102007019554 A1 11/2008

(Continued)

OTHER PUBLICATIONS

Suri, "White Matter/Gray Matter Boundary Segmentation Using Geometric Snakes: A Fuzzy Deformable Model", Singh, et al. (Eds.): ICAPR 2001, LNCS 2013, pp. 331-338, 2001.*

(Continued)

Primary Examiner — Luke Gilligan
Assistant Examiner — Robert Sorey
(74) Attorney, Agent, or Firm — Harness, Dickey & Pierce

(57) ABSTRACT

A method is disclosed for determining a 2D contour of a vessel structure imaged in 3D image data for a first slice plane of the vessel structure, wherein the 3D image data was generated using a medical imaging system and has a multiplicity of image voxels which are all assigned a respective image value. In at least one embodiment, the method includes providing 3D image data; determining a multiplicity of first initial 2D contours of the vessel structure, wherein the first initial 2D contours in the 3D image data are determined for slice planes of the vessel structure, which planes are arranged orthogonally in respect of a central line of the vessel structure and spaced apart from one another along the central line; determining a first initial 3D contour from the first initial 2D contours; determining a smoothed second 3D contour by applying an active 3D contour model to the first initial 3D contour; determining a second initial 2D contour as a slice through the smoothed second 3D contour including the first slice plane; and determining the 2D contour by iteratively fitting the second initial 2D contour to that vessel structure imaged in the 3D image data which results for the first slice plane.

18 Claims, 7 Drawing Sheets

(56) References Cited

U.S. PATENT DOCUMENTS

| | | | |
|---|---|---|---|
| 2003/0053669 A1* | 3/2003 | Suri et al. | 382/130 |
| 2004/0151356 A1* | 8/2004 | Li et al. | 382/131 |
| 2005/0041842 A1* | 2/2005 | Frakes et al. | 382/128 |
| 2006/0078181 A1* | 4/2006 | Chen et al. | 382/128 |
| 2006/0262988 A1 | 11/2006 | Tek et al. | |
| 2007/0116342 A1* | 5/2007 | Zarkh et al. | 382/130 |
| 2007/0248250 A1* | 10/2007 | Gulsun et al. | 382/128 |
| 2008/0123914 A1* | 5/2008 | De Bliek et al. | 382/128 |
| 2008/0137926 A1* | 6/2008 | Skinner et al. | 382/131 |
| 2008/0292194 A1* | 11/2008 | Schmidt et al. | 382/217 |
| 2009/0310835 A1* | 12/2009 | Kaus et al. | 382/128 |

FOREIGN PATENT DOCUMENTS

| | | |
|---|---|---|
| WO | WO-2005055126 A1 | 6/2005 |
| WO | WO 2005055126 A1 | 6/2005 |
| WO | WO 2007058632 A1 * | 5/2007 |

OTHER PUBLICATIONS

Kyungha Min, Yoo-Joo Choi. "Adaptive reconstruction of pipe-shaped human organs from 3D ultrasonic volume," Computerized Medical Imaging and Graphics: The Official Journal of the Computerized Medical Imaging Society, Mar. 1, 2006, vol. 30, Issue 2: pp. 109-121.*

M. Kass, A. Witkin, D. Terzopoulos; Snakes: Active Contour Models, International Journal of Computer Vision. 321-331 (1988), 1987 Kluwer Academic Publishers, Boston, Manufactured in the Netherlands; Publikatlon "A Note on Two Problems in Connexion with Graphs", Numerische Mathematik 1, Selten 269-271, 1959; Others.

Duddalwar, VA. "Multislice CT angiography: a practical guide to CT angiography in vascular imaging and Intervention", The British Journal of Radiology, 77 (2004), pp. S27-S38; Others.

De Bruijne M et al.: "Interactive segmentation of abdominal aortic aneurysms in CTA Images" Medical Image Analysis, vol. 8, Issue2, Jun. 2004; Others.

Greiner K et al.: "Segmentierung von Aortenaneurysmen in CTA-Bildem mlt dem statistischen Verfahren der Active Appearance Models" Bildverarbeitung für die Medizin, Apr. 2008; Others.

Milwer MB et al.: "Fast-marching contours for the segmentation of vessel lumen in CTA cross-sections" IEEE-EMBS 2007. Aug. 22-26, 2007, Lyon. pp. 791-794; Others.

M. Kass, A. Witkin, D. Terzopoulos; Snakes: Active contour Models, International Journal of Computer Vision, 321-331 (1988), 1987 Kluwer Academic Publishers, Boston, Manufactured in the Netherlands; Publication, "A Note on Two Problems in Connection with Graphs", Numerische Mathematik 1, Seiten 269-271, 1959; Others.

Duddalwar, VA, "Multislice CT angiography: a practical guide to CT angiography in vascular imaging and intervention", The British Journal of Radiology, 77 (2004), pp. S27-S38; Others.

De Bruijne M. et al.: Interactive segmentation of abdominal aortic aneurysms in CTA images:, Medical Image Analysis, vol. 8, Issue2, Jun. 2004; Others.

Greiner K et al.: "Segmentierung von Aortenaneurysmen in CTA-Bildern mit dem statistischen Verfahren der Active Appearance Models", Bilderarbeitung für die Medizin, Apr. 2008; Others.

Milwer MB et al.: "Fast-marching contours for the segmentation of vessel lumen in CTA cross-sections", IEEE-EMBS 2007, Aug. 22-26, 2007, Lyon. pp. 791-794; Others.

Yang Y et al.: "Automatic Segmentation of Coronary Arteries using Bayesian Driven Implicit Surfaces" IEEE-ISBI 2007, pp. 189-192; Others.

Yang Y: "Image Segmentation and Shape Analysis of Blood Vessels with Applications to Coronary Atherosclerosis" PhD-Thesis, Georgia Institute of Technology, May 2007; Others.

* cited by examiner

METHOD FOR DETERMINING A 2D CONTOUR OF A VESSEL STRUCTURE IMAGED IN 3D IMAGE DATA

PRIORITY STATEMENT

The present application hereby claims priority under 35 U.S.C. §119 on German patent application numbers DE 10 2008 063 326.7 filed Dec. 30, 2008 and DE 10 2009 006 636.5 filed Jan. 29, 2009, the entire contents of each of which are hereby incorporated herein by reference.

FIELD

At least one embodiment of the present invention lies generally in the field of medical technology and generally describes a method for determining a 2D contour of a vessel structure imaged in 3D image data for a first slice plane of the vessel structure. An important field of application of at least one embodiment of the method is the analysis and diagnosis of vessel diseases on the basis of medical 3D image data, particularly in connection with cardiovascular diseases.

BACKGROUND

In modern medicine, local vessel diseases of patients, in particular stenoses, aneurysms and dissections, are usually diagnosed on the basis of 3-dimensional image data (3D image data) generated by computed tomography angiography (CTA). In order to acquire such 3D image data, the body region of interest of the patient is scanned in three dimensions by a computed tomography scanner after a contrast agent has been injected into the veins. The measured values acquired in the process are calculated and are made available for viewing or further evaluation as 3D image data or as 2D image data determined therefrom. Administering the contrast agent is necessary for there to be contrast between the blood vessels and the surrounding tissue. The lumen of the arteries, which is enriched by the contrast agent and therefore seems to be bright in the 3D CTA image data, can thus be evaluated and measured more easily.

It is typically a radiologist at a post-processing workstation who evaluates, analyzes and diagnoses vessel structures imaged in 3D image data. Various evaluation and imaging methods for vessel analysis are available these days. Inter alia, these include so-called maximum intensity projection (MIP) methods, volume rendering (VR) methods, multiplanar reconstruction (MPR) methods or curved planar reconstruction (CPR) methods, which are explained in more detail in, inter alia, the review article by Duddalwar V A, "Multislice CT angiography: a practical guide to CT angiography in vascular imaging and intervention", The British Journal of Radiology, 77 (2004), pages S27-S38.

Key to the analysis of vessel diseases is the precise determination of 2D contours (contour lines) of the vessel structure imaged in the 3D image data, said contours for slice surfaces (cross-sectional surfaces) arranged orthogonally with respect to the central line being determined along a central line of the vessel structure. This is because only the precise knowledge of the 2D contours subsequently affords the possibility of exactly determining along the vessel the variables important for blood flow through said vessel: the minimum and maximum diameter of the vessel cross section, and the cross-sectional area. If, from the 3D image data for all central line points, corresponding 2D contours are determined, measured and plotted along the central line, the diameter or the cross-sectional area profile, for example, along the vessel can be illustrated graphically as a so-called vessel profile. Here, local minima along the profile of the profile curve indicate a stenosis and maxima indicate potential aneurysms. Moreover, the form of the disease can also be analyzed in more detail in the views; for example, the presence of calcifications or thrombotic structures can be inferred from the intensity of plaques and these can for example indicate the infarct risk of a patient.

These days, different methods for determining 2D contours in a vessel structure imaged in 3D image data are known.

A simple and often utilized algorithm for determining 2D vessel contours is the tracking of the outer edge of regions of related pixels, with the brightness of said pixels lying between an upper and a lower threshold. This approach lends itself in particular to the evaluation of CTA images since the brightness of the pixels is calibrated for every computed tomography scanner and can thereby be measured as an equipment-independent CT value.

The CT values indicate which tissue structure is imaged in the examined image region. Table 1 shows the identifying CT values for some tissue types. (cf. Table 1).

TABLE 1

| Tissue type | CT Values |
| --- | --- |
| Bone | >250 |
| Thyroid | 70 ± 10 |
| Liver | 65 ± 5 |
| Spleen | 45 ± 5 |
| Pancreas | 45 ± 5 |
| Kidney | 40 ± 10 |
| Fat | −90 ± 10 |
| Blood | 55 ± 5 |
| Gray matter | 30 ± 4 |

However, the quality of 2D contours determined by pure threshold-based evaluation methods in the 3D image data is very limited due to the following properties of CTA image data:

a) Arteries are often surrounded by similarly bright regions (i.e. by regions which have similar CT values), for example adjacent vessel structures, veins, bones and cartilage, calcifications, image artifacts, exsanguinations, etc.

b) As a result of image noise and an unevenly distributed contrast agent, there are intensity variations within the lumen enriched by the contrast agent.

If, for example, the lower threshold is set to be too low in such threshold-based evaluation methods, adjacent 3D image data regions merge and so the 2D contour determined thereby also includes these adjacent regions. This overestimates the vessel cross section which in individual cases falsifies vitally important measurement results. This disadvantageous effect particularly occurs when the spatial distance between the vessel structure of interest and the surrounding structures with similar CT values is less than the resolution of the imaging chain through the computed tomography scanner.

Alongside these methods, purely gradient-based evaluation methods are known and these detect the 2D contours solely on the basis of locally strongly pronounced changes in image values (grayscale values) without considering the absolute image values. However, these evaluation methods are very sensitive to image noise. Depending on the parameterization in the imaging and in the contrast agent distribution, there is different development of noise in the 3D image data. The image noise often generates pseudo-contours and so the purely gradient-based evaluation methods generally supply 2D contours of lower quality than threshold-based methods.

The document U.S. Pat. No. 6,782,284 B1 discloses a method for semi-automatic measurement of aneurysms and for planning surgical procedures connected to inserting synthetic stents into blood vessels. The method is based on evaluating provided 3D image data from medical imaging equipment, in which blood vessels are imaged. The method comprises the method steps of: identifying a blood vessel type, receiving vascular landmarks from an assigned user, extracting an orthogonal vessel plane, localizing a vessel center in the vessel plane, fitting vessel boundaries in the vessel plane and recursive repetition of the above method steps.

The document U.S. Pat. No. 6,643,533 B2 discloses a method for displaying tubular structures which are imaged in a medical 3D image data record. The method comprises the method steps of: determining a vessel central line; determining a vessel contour in a plane, with the plane being arranged orthogonally with respect to the vessel central line at a selected point of the vessel central line; determining the lengths of a multiplicity of segments which extend along the vessel structure and pass through the selected point; selecting a segment from the multiplicity of segments; and displaying an image plane which is defined by the selected segment and an axis which runs tangentially in respect of the vessel central line at the selected point.

The document DE 10 2007 019 554 A1 discloses a method based on volume data for the two-dimensional display of elongate lumen structures in a patient. The method comprises the following method steps: receiving tomographic volume data on the basis of a scan of the examination object and reconstructing detector data; segmenting at least one elongate hollow organ; automatically determining a start position and a start direction or receiving a manually defined start position or start direction; providing a multiplicity of 2D slice images along the elongate hollow organ; and emitting the 2D slice images of the hollow organ in the sequence of a virtual endoscopy.

SUMMARY

In at least one embodiment of the present invention, an efficient method is afforded for determining a 2D contour of a vessel structure imaged in 3D image data. In the process, at least one of the abovementioned disadvantages should be avoided as far as possible. In particular, compared to the prior art, the same or an increased accuracy in determining the 2D contour should be possible in at least one embodiment, whilst having reduced computational complexity.

The method according to at least one embodiment of the invention for determining a 2D contour of a vessel structure imaged in 3D image data for a first slice plane of the vessel structure, wherein the 3D image data was generated using a medical imaging system and has a multiplicity of image voxels which are all assigned a respective image value, comprises the following steps:

1.1 providing 3D image data,
1.2 determining a multiplicity of first initial 2D contours of the vessel structure, wherein the first initial 2D contours in the 3D image data are determined for slice planes of the vessel structure, which planes are arranged orthogonally in respect of a central line of the vessel structure and spaced apart from one another along the central line,
1.3 determining a first initial 3D contour from the first initial 2D contours,
1.4 determining a smoothed second 3D contour by applying an active 3D contour model to the first initial 3D contour,
1.5 determining a second initial 2D contour as a slice through the smoothed second 3D contour including the first slice plane and
1.6 determining the 2D contour by iteratively fitting the second initial 2D contour to that vessel structure imaged in the 3D image data which results for the first slice plane.

In this document, the term "contour" is used for a two-dimensional contour line (2D contour) and a three-dimensional surface (3D contour) of a three-dimensional structure. Here, a 2D contour (intersection) results as a slice of the surface of a three-dimensional structure in a slice plane. In at least one embodiment of the present case, such three-dimensional structures are the vessel structure imaged in the 3D image data and the first initial and smoothed second 3D contour, with the latter two each being a three-dimensional (mathematical) model of the vessel structure imaged in the 3D image data. Thus, in at least one embodiment of the present case, the 2D contours (contour lines) represent points in the vessel wall of the vessel structure. The present problem when determining the first initial 2D contours and when determining the 2D contour is fitting, as accurately as possible, these 2D contours to the vessel structure imaged in the 3D image data. Here, recognizing the respective vessel wall bounding the lumen of the vessel structure plays an important role.

The term "initial" indicates that these are approximations which are fitted iteratively, i.e. improved, over the course of the method.

In step 1.1, the 3D image data is provided, for example, on a storage unit of a post-processing workstation, preferably in the memory thereof. The 3D image data is preferably three-dimensional CTA image data. However, the method can also be applied to 3D image data from other medical imaging systems, such as, for example, a CT, MRI, PET, SPECT or a duplex sonography system.

In step 1.2, a multiplicity of first initial 2D contours of the vessel structure are determined, wherein the first initial 2D contours in the 3D image data are determined for slice planes of the vessel structure, which planes are arranged orthogonally in respect of a central line of the vessel structure and spaced apart from one another along the central line. Hence, each of the first initial 2D contours represents an initial 2D model for the respective slice plane, that is to say an approximation of the corresponding 2D vessel contour which results as a slice of this slice plane with the vessel structure imaged in the 3D image data.

The first initial 2D contours are preferably determined by an evaluation method based on thresholds and/or gradients. Additionally, or alternatively, it is possible for one or more active 2D or 3D contour models, preferably an active threshold-based 2D or 3D contour model, to be applied for determining or optimizing the first initial 2D contours.

Such active contour models (ACM), which are also referred to as "SNAKES" methods, are known to a person skilled in the art from the prior art. In general, an active contour model comprises nodes and edges with variable lengths or splines. Using an iterative optimization, the nodes of a 2D or 3D contour are displaced such that an energy term is minimized. This energy term consists of a weighted sum of internal and external energy. The internal energy is used for smoothing and assumes its minimum in the case of a circular shape. The external energy is based on the gradient of the image values of the 2D or 3D image data; the high value in that case indicates where there are discontinuities in the image values. The prior art comprises a multiplicity of descriptions for active contour models. As a representative for these descriptions, reference is made here to the publication by Kass M, Witkin A and Terzopoulos D, "Snakes: Active contour models", International Journal of Computer Vision, Vol. 1, No. 4, January 1988, the entire contents of which are hereby incorporated herein by reference.

In a particularly preferred variant of the method according to at least one embodiment of the invention, a number n of contour points are determined for each slice plane in step 1.2 by evaluating the 3D image data, wherein each of the first initial 2D contours results in a closed continuous line, for example in the form of a polygon, which connects the contour points determined.

In a further an example embodiment variant of the method, image values of image voxels, which respectively lie on one of n rays emanating radially from the central line are evaluated in order to determine the n contour points per slice plane in the 3D image data, wherein the n rays lie in the slice plane and have an angular distance from one another, in particular a constant angular distance, e.g. 360°/n; the evaluation of the image values starting at the central line continues radially outward along the rays; and a contour point is detected on one of the n rays if the image value of an image voxel satisfies a predetermined criterion, in particular a threshold or gradient criterion.

In order to limit the computational complexity, the image values along the n rays can in each case only be evaluated up to a radius R starting from the central line. If no contour point is recognized up to the radius R for one of the n rays emanating from the central line because the predetermined criterion thereof was not satisfied by the corresponding image values, a contour point is assigned on this ray at a distance R from the central line.

The slice planes are preferably arranged at a constant spacing along the central line.

In step 1.3, a first initial 3D contour is determined from the first initial 2D contours. This is preferably effected using a triangulation method. Such triangulation methods are known in the prior art. The first initial 3D contour thus represents a first three-dimensional (mathematical) initial (e.g. tube-) model of the vessel structure imaged in the 3D image data, i.e. of the vessel walls thereof.

In step 1.4, the first initial 3D contour is iteratively fitted to the vessel structure imaged in the image data. In the process, a smoothed second 3D contour is determined by applying an active 3D contour model to the first initial 3D contour. For an explanation of the term "active 3D contour model", reference is made to the abovementioned explanations in this respect.

In step 1.5, a second initial 2D contour is determined as a slice through the smoothed second 3D contour including the first slice plane. In this case, the first slice plane is preferably arranged orthogonally in respect of the central line; furthermore, it preferably corresponds to one of the slice planes from step 1.2. As a result of step 1.5, first initial 2D contours which are, for example, determined ambiguously in step 1.2 can be optimized by utilizing the spatial relationship with adjacent first initial 2D contours. However, this approximate second initial 2D contour is not sufficiently accurate for most applications and so further processing steps for refining and adjusting the second initial 2D contour are required for determining the 2D contour.

In step 1.6, the 2D contour is determined by iteratively fitting the second initial 2D contour to that vessel contour imaged in the 3D image data which results for the first slice plane. In the process, it is preferable for a threshold-based and/or gradient-based evaluation method to be applied. It is particularly preferable for one or more threshold-based active 2D contour models to be applied in step 1.6, in particular an active 2D contour model based on an unmonitored learning edge model.

In an example embodiment variant of the method according to the invention, step 1.6 comprises the following steps as per claim 15: In step 15.1, the second initial 2D contour is fitted using a threshold-based active 2D contour model. In respect of the active 2D contour model, reference is once again made to the explanations above. In step 15.2, contour points and/or contour sections are determined which were not fitted in a satisfactory fashion in step 15.1. As a result of this, those contour points and/or contour sections which have already achieved a satisfactory fit are likewise known in step 15.1. In step 15.3, an active 2D contour model based on an unmonitored learning edge model is applied to the contour points and/or contour sections determined in step 15.2, wherein training data for the unmonitored, i.e. autonomous, learning 2D contour model is determined from already satisfactorily fitted contour points and/or contour sections from step 15.1.

In this case, the method steps 15.1 to 15.3 are preferably performed iteratively for an increasing number of contour points n until a predetermined accuracy of the fit of the second initial 2D contour to the vessel structure imaged in the 3D image data is achieved.

The method according to at least one embodiment of the invention can also be repeated, starting with step 1.5, after carrying out step 1.6, with a different first slice plane being predetermined in each case. This affords the possibility of determining profiles, e.g. of the vessel cross section, along the central line.

In the method according to at least one embodiment of the invention, a 2D contour, refined in 2 dimensions, is firstly determined as a three-dimensional structure from the 3D image data and is used as an initialization for the 2-dimensional contour as a result of a slice including the first slice plane.

The method according to at least one embodiment of the invention achieves desired outcomes in a simple and fast manner whilst using one or more active contour models (ACM). In the process, ambiguous determined first initial 2D contours in particular can be determined unambiguously by utilizing the spatial relationship with spatially adjacent first initial 2D contours.

BRIEF DESCRIPTION OF THE DRAWINGS

The invention will be explained in more detail in the following text on the basis of an example embodiment and the associated figures, in which FIG. 9)

DETAILED DESCRIPTION OF THE EXAMPLE EMBODIMENTS

Figure 1:
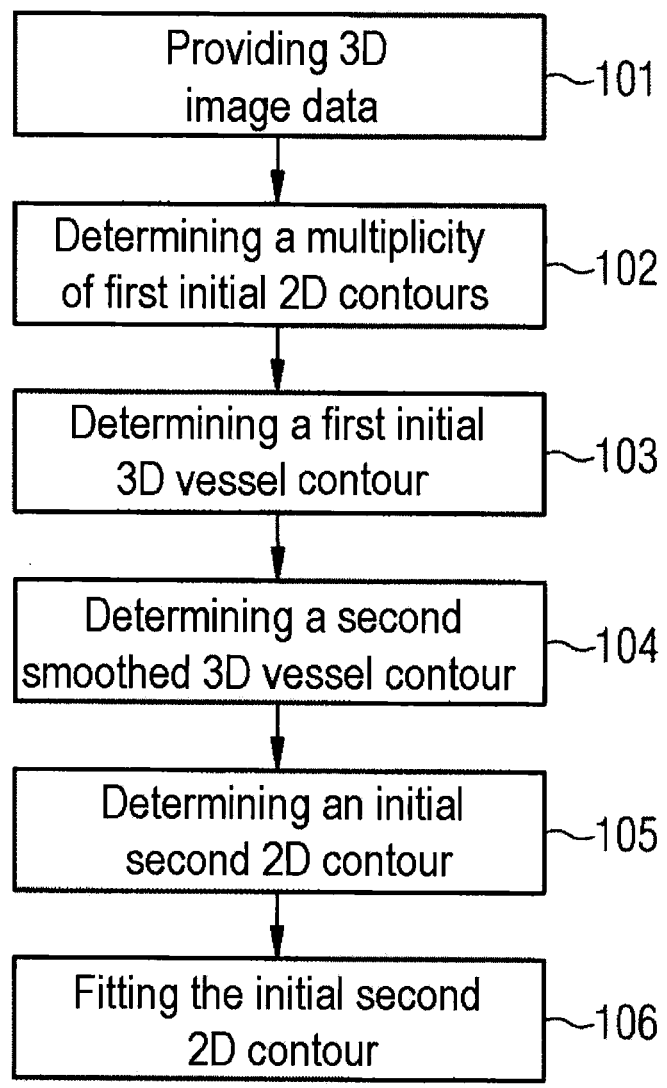
FIG. 1 shows a general progression of the method according to an embodiment of the invention in a schematic illustration.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows the general progression of the method according to an embodiment of the invention. The method steps 101 to 106 correspond to the method steps 1.1 to 1.6 as per claim 1.

In the present example embodiment, 3D CTA image data is provided in step 101. A vessel structure is imaged in the 3D image data. An object of an embodiment of the method is to fit as precisely as possible a 2D contour 14 for a first slice plane 9 to the corresponding vessel contour in the image data.

A multiplicity of first initial 2D contours 16 of the vessel structure are determined in step 102, wherein the first initial 2D contours 16 are determined in the 3D image data for slice planes 2 of the vessel structure, which planes are arranged orthogonally in respect of a central line 1 of the vessel structure and spaced apart from one another along the central line 1. To this end, the central line 1 of the vessel structure imaged in the 3D image data is determined in a step referred to as 102a in the text. A person skilled in the art is aware of appropriate methods from the prior art.

Figure 3:
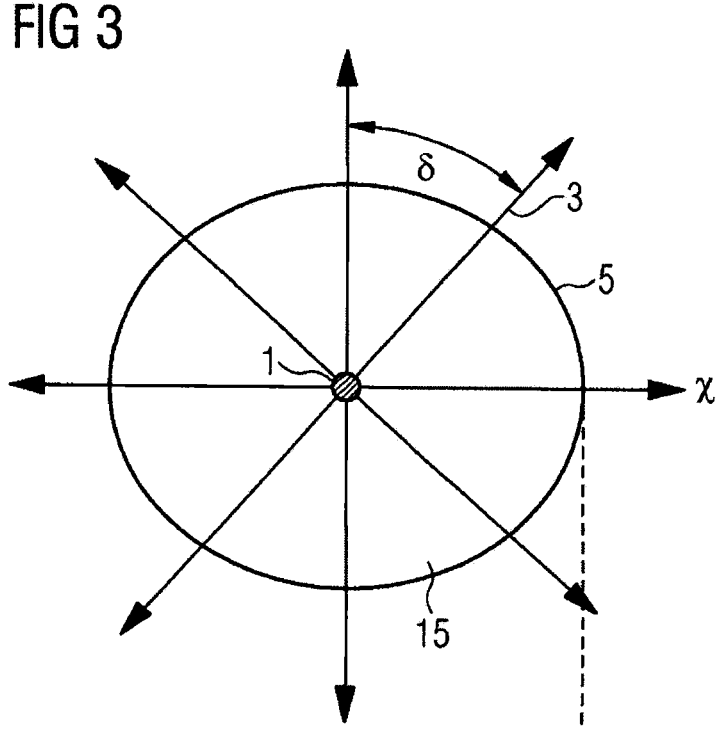
FIG. 3 shows a schematic illustration for explaining how to determine the first initial 2D contours.

In a step referred to by 102b in the text, a number n of contour points $P_i$, i=1, ..., n are determined for each slice plane 2 by evaluating the 3D image data, wherein each of the first initial 2D contours result in a closed continuous line which connects the contour points $P_i$ determined for the respective slice plane 2. For this, as illustrated in FIG. 3, image values of image voxels are evaluated per slice plane 2, which respectively lie on one of n rays 3 emanating radially from the central line 1, wherein the n rays 3 (n=8 in FIG. 3) lie in the respective slice plane 2 and have a constant angular distance δ from one another. The evaluation of the image values (CT values) in each case starts at the central line 1 and continues radially outward along the n rays 3, with a contour point $P_i$ being detected on a ray 3 if the image value of an image voxel satisfies a predetermined criterion, in particular a threshold criterion or gradient criterion.

Figure 4:
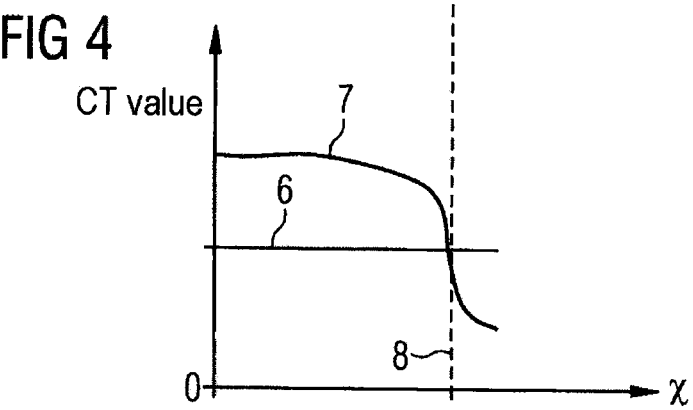
FIG. 4 shows a graph which plots the profile of the image values (CT values) for image voxels lying on one of the n rays.

FIG. 4 shows a graph which plots the radial distance from the central line 1 along the x-axis and the image values (CT values) of the image values along the y-axis. Hence, the curve 7 represents the brightness profile along a ray 3. In order to identify a contour point $P_i$, an interval 6, bounded above and below by a threshold, is predetermined in the present case. Using this, a contour point $P_i$ is detected if the upper threshold is exceeded or if the value drops below the lower threshold. In FIG. 4, the brightness profile (CT values) falls below the lower threshold 6 at the x-coordinate 8 and so a contour point is detected at that location. The brightness profiles (also referred to as image value profiles, CT value profiles) are thus analyzed along the n rays per slice plane 2, and in each case n contour points are determined. As an alternative to evaluating the brightness profiles on the basis of threshold value criteria, it is possible, for example, for gradient criteria or a mixture of threshold and gradient criteria to be applied for determining the contour points $P_i$. As a result, a number n of contour points $P_i$ is determined for each slice plane 2 by evaluating the 3D image data, wherein each of the first initial 2D contours 16 results in a closed continuous line which connects the contour points $P_i$ determined for the respective slice plane 2.

This methodology (steps 102a and 102b) for identifying contour points $P_i$ has outliers, particularly in the region of vessel branching (or in the case of two closely adjacent vessels), at which the spacing of contour points $P_i$, adjacent in a slice plane 2, can differ significantly. Moreover, the surface of the vessel has not yet been reached in all cases because the evaluation along the rays is limited by a predefined length R. This length R is preferably selected to be optimized in such a fashion that, on the one hand, the required calculation time for the evaluation is minimized and, on the other hand, the success probability for a contour point does not drop below a predetermined value.

A first initial 3D contour 4a is determined from the first initial 2D contours 16 in step 103. An interpretation of the present points as a closed 3D contour can preferably be effected by triangulation.

Figure 2:
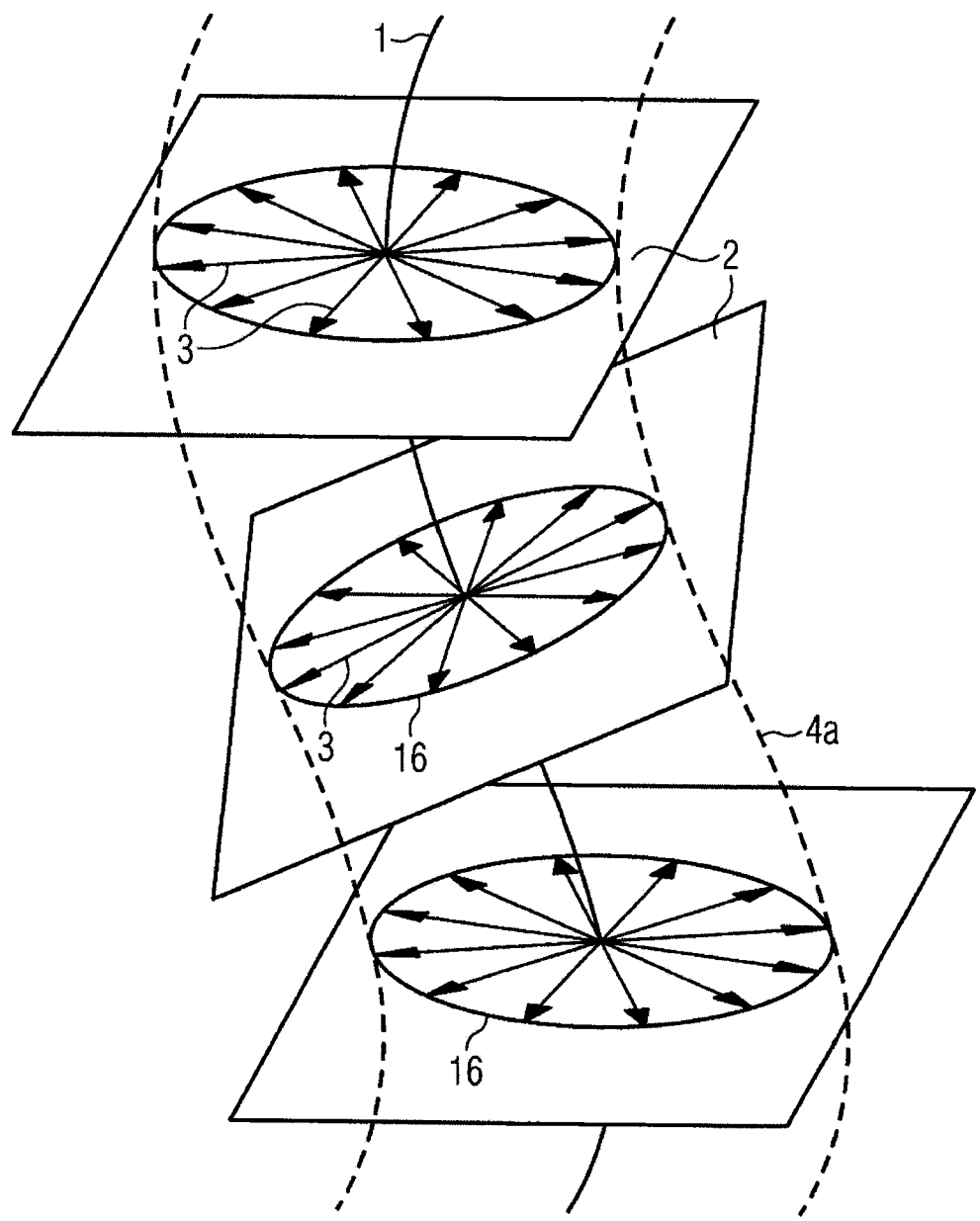
FIG. 2 shows a schematic illustration for explaining how to determine the first initial 3D contour.

FIG. 2 schematically shows the result of steps 101 to 103. In these steps, first initial 2D contours 16 were determined by way of search rays 3 for a multiplicity of slice planes 2 standing orthogonally on the central line 1. A first initial 3D contour 4a was determined in step 103 by triangulation based on the determined first initial 2D contours 16.

Figure 7:
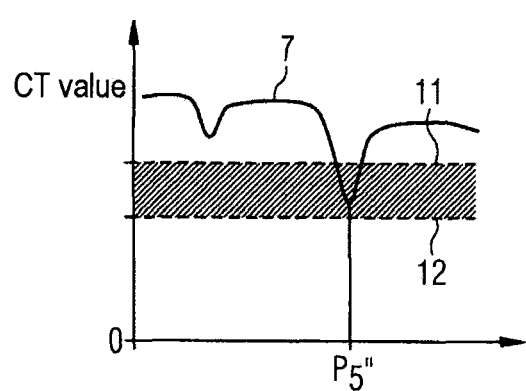
FIG. 7 shows the profile of the image values (CT values) along the fifth ray (1->$P_5'$) in FIG. 6.

In order to improve the result of the above determination of the first initial contour points $P_i$ or of the first initial 3D contour 4a determined therefrom for forming the smoothed second 3D contour 4b, the first initial 3D contour 4a determined above is furthermore iteratively fitted to the 3D image data by way of an additional threshold-based active contour model (ACM method). Analogously to the above threshold-based method, an interval is used [lower interval value 12, upper interval value 11; c.f. FIG. 7].

Each iteration step in respect thereof in this example embodiment comprises two further method steps (referred to as 104a and 104b in the text):

There is an outward displacement of each previously determined contour point $P_i$ along the respective ray 3 in step 104a. Starting from the central line 1, there is in turn an analysis of the brightness values along each ray 3, the analysis detecting whether a predetermined brightness interval is left. If a threshold criterion is satisfied in the process, a new contour point $P_i'$ is obtained in each case (it corresponds to the contour point $P_i$ displaced toward the outside). However, the displacement is limited and so a new contour point $P_i'$ does not necessarily come to rest on the surface of the vessel structure in every case.

Figure 5:
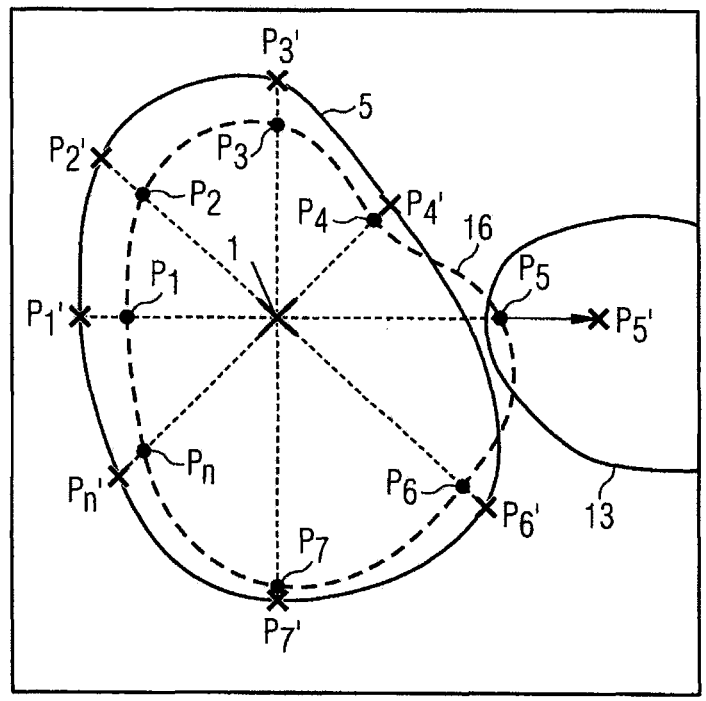
FIG. 5 shows a schematic illustration for explaining how the contour points $P_i$ (i=1, . . . ,n) of a first initial 2D contour are fitted to a vessel contour.

To this end, FIG. 5 shows a result of step 104a. A cross section of the vessel, the 2D contour of which is intended to be determined, and the cross section of an adjacent vessel 13 can be gathered from FIG. 5. Eight rays starting from the central line 1 are plotted. Furthermore, the first initial 2D contour 16, determined above in steps 102a and 102b on the basis of the contour points $P_i$, is plotted as a dashed closed line, which contour should now be fitted iteratively to the vessel contour 5 in an improved fashion. By displacing the contour points $P_i$ determined above toward the outside or by the associated evaluation of the corresponding image values, the contour points $P_1'$ to $P_4'$, and $P_6'$ to $P_8'$ were optimally fitted to the vessel contour 5 in step 104a. It is only the point $P_5'$ which does not lie on the vessel wall of the vessel cross section 5; rather, it lies within the adjacent vessel 13. In the present case, the point $P_5'$ results from, on the one hand, the contour point $P_5$ being incorrectly determined in the preceding steps 102a and 102b since it already lies within the adjacent vessel 13 and, on the other hand, from the limited displacement of the contour points $P_i$ and so the contour point $P_5'$ comes to rest within the vessel 13, although no triggering threshold criterion has been satisfied.

In step 104b, a simple outlier test is performed. To this end, the image values (CT values) are analyzed along the n rays, starting from the central line 1 and going up to the points $P_i'$ determined in step 104a; this analysis is performed to detect possible dark tissue structures which delimit the vessel of interest lying between the central line 1 and the points $P_i'$. To this end, a further criterion is used to detect contour points in addition to an upper threshold $S_o$ and a lower threshold $S_u$ 6; the further criterion replacing the lower threshold 6 by an interval with a lower interval boundary 12 and an upper interval boundary 11. Within this interval, an image value is recognized as being a contour point if it is either darker than the previous image value (first derivation) by the standard deviation σ determined along the ray 3 up until this point, or if it lies outside of the interval [μ−3σ, μ+3σ] which constitutes a statistically significant deviation from the mean μ, which is very likely not to have been caused by noise (c.f. the six sigma method), where μ is the mean determined along the ray and σ is the standard deviation of the image values determined along the ray.

Figure 6:
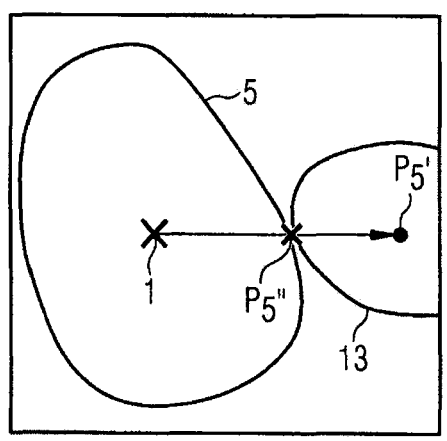
FIG. 6 shows a schematic illustration which, in conjunction with FIG. 7, explains how outliers, e.g. the contour point $P_5'$ illustrated in FIG. 5, are recognized.

FIG. 6 shows the situation of FIG. 5 for the fifth ray which emanates from the central line 1 and leads up to the contour point $P_5'$. Moreover, the new contour point $P_5''$ has been determined as a result of step 104b.

Analogously to FIG. 4, FIG. 7 shows a graph in which the x-axis specifies the radial distance from the central line 1 and the y-axis specifies the image values (CT values). The curve 7 in this case represents the image values (brightness values) along the fifth ray from the central line 1 up to the contour point $P_5'$. In the graph, the region between the upper interval value 11 and the lower interval value 12 can be removed as the shaded area in which the above-described analysis of the image values lying there is undertaken. By evaluating the image values lying in the interval according to the above-described method, the new, correct contour point $P_5''$ can be determined in the present case.

The second initial 3D contour 4b is smoothed by minimizing the internal energy of the utilized active contour model in every fitting step. In the process, the contour profile through the contour points $P_i$ of the first initial 2D contours 16 is smoothed by the simulation of the property of an elastic material using a numerical method. This corresponds to a solution of a linear system of equations with a stiffness matrix, similar to the finite element method.

As a result of the smoothing in 3-dimensional space, the first initial 3D contour 4a is consistently fitted to the 2D contours appearing in adjacent slice planes 2. Subsequently, a second 3D contour 4b without significant outliers (like a tube around the vessel), which is smoothed in an approximate fashion over the vessel profile in 3-dimensional space, is present.

Figure 8:
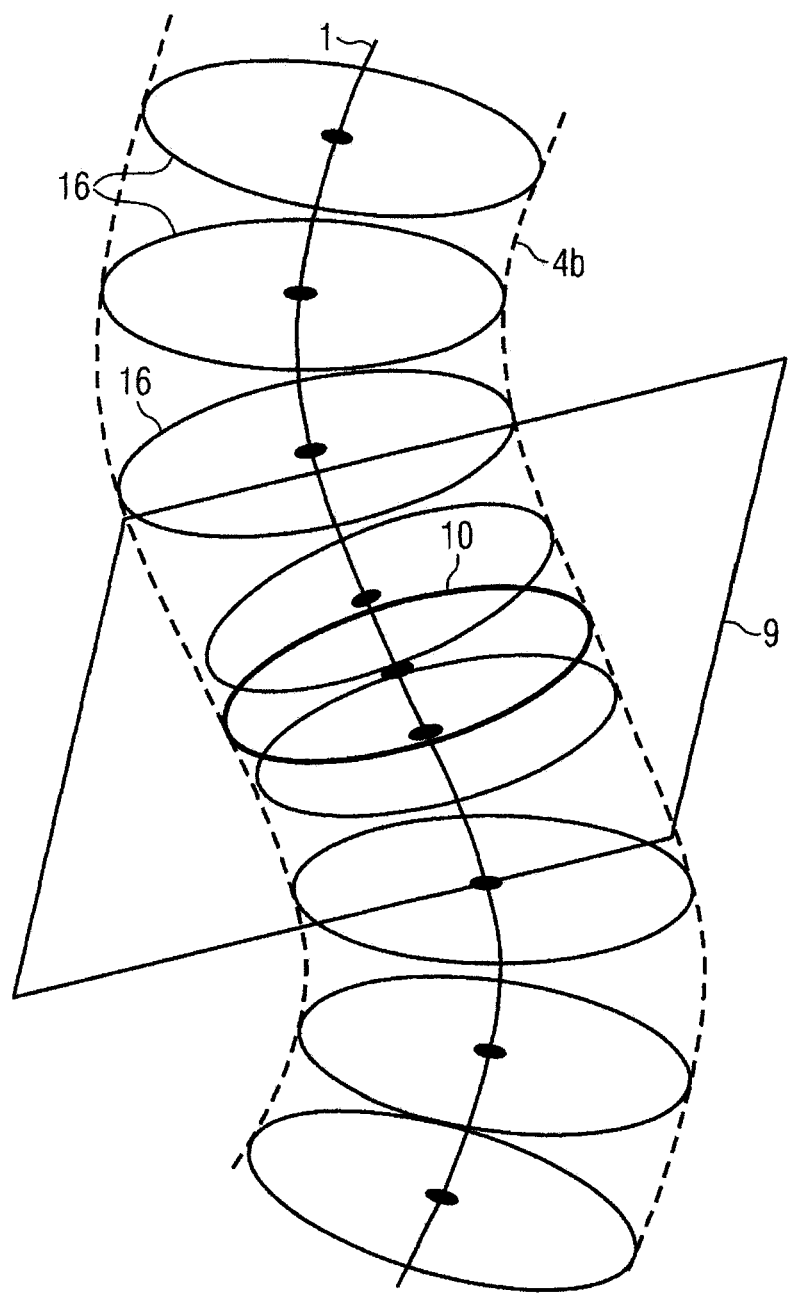
FIG. 8 shows a schematic illustration for determining the second initial 2D contour by calculating the slice between the smoothed second 3D contour and the first slice plane, wherein the second 2D initial contour is used for initializing the subsequent two-dimensional active contour model.

In step 105, a second initial 2D contour 10 is determined as a slice through the smoothed second 3D contour 4b including the first slice plane 9. This is illustrated in FIG. 8. The smoothed second 3D contour 4b can be gathered from FIG. 8, said 3D contour being based on the multiplicity of first initial 2D contours 16 for slice planes standing orthogonally in respect of the central line 1. The second initial 2D contour 10 is calculated by a slice through the smoothed second 3D contour 4b including the first slice plane 9.

However, for most applications, this approximate second initial 2D contour 10 is not sufficiently accurate and so this is followed by a further processing step for refining and adjusting said contour.

In step 106, the 2D contour 14 is determined by iteratively fitting the second initial 2D contour 10 to that 2D contour 5 of the vessel structure imaged in the 3D image data which results for the first slice plane 9. In the present example embodiment, a few iterations with active contour models, operating on different principles and described in the following sub-steps, are respectively carried out in this case.

First of all, threshold-based fine fitting of the second initial 2D contour 10 to the 3D image data is performed in a step referred to by 106a in the text. In the process and using an active 2D contour model, the second initial 2D contour 10 is fitted to the vessel contour in the first slice plane 9 in the 3D image data in only a few iterations using search rays, which run in the first slice plane 9 and originate from the central line 1, by only considering upper and lower threshold $S_o$, $S_u$. In the process, outliers can once again occur, or outliers which had not been eliminated by one of the preceding steps can be amplified.

In a step referred to by 106b in the text, outliers are identified and eliminated. In the preceding step 106a, a record was made for each contour point of the fitted second initial 2D contour as to whether a position on the vessel contour had already been found (i.e. the last examined ray left the threshold range) after a fixed number of iterations. These contour points now remain unchanged in this step 106b. However, contour points which do not yet lie on the surface of the vessel, for example because the image values of the last examined ray all lie within the threshold range, are fitted to the image data using an edge model which was learnt in an unmonitored fashion in this step 106b. To this end, a plurality of sub-steps are once again required (referred to as 106ba, 106bb, 106bc in the text).

In step 106ba, an edge model is learnt using the contour points already correctly fitted in step 106a. Image value profiles (CT profiles) are extracted along search rays which are emitted from the center 1 of the vessel contour 5 up to each contour point. The mean profile of the edges determined in the image value profiles results in the unmonitored learnt edge model. Hence, each iteration results in a correspondingly refined edge model.

Figure 9:
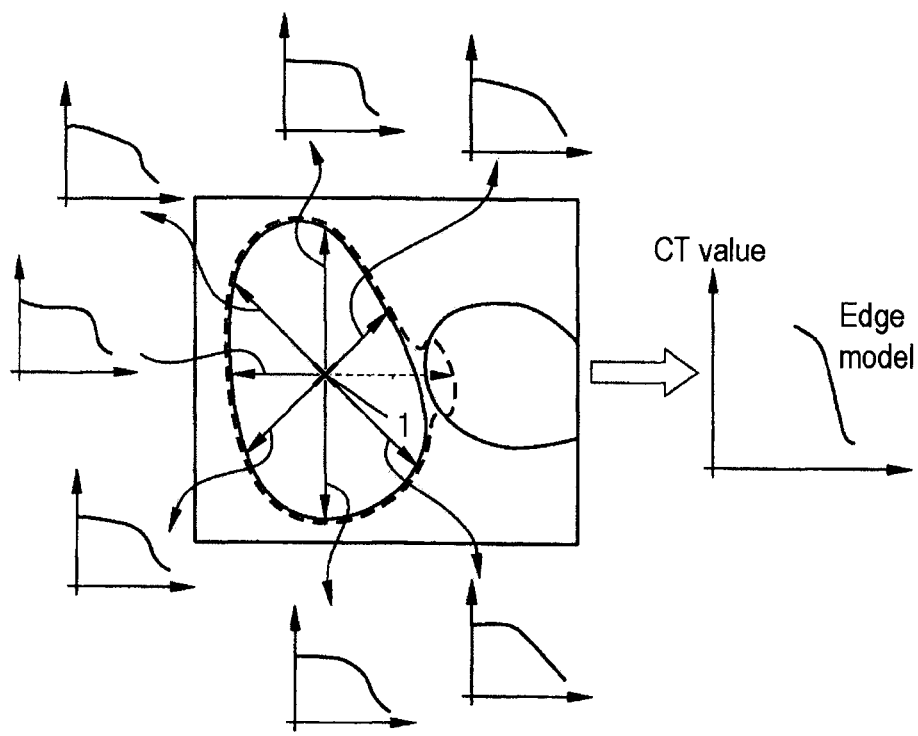
FIG. 9 shows a schematic illustration for demonstrating the unmonitored learning edge model as averaged profile of the image value edges (CT values) determined along the n rays.

To this end, FIG. 9 shows the respectively determined CT value profiles along the respective rays for seven contour points which have already been correctly fitted. The learnt edge model illustrated on the right-hand side in FIG. 9 is determined from these seven profiles as a mean image value profile.

In a further step 106bb, the number of contour points which still have to be fitted is determined from the number of contour points which have not yet been fitted completely by combining the latter in clusters. Clusters lying close to one another are in each case merged into one cluster. Moreover, the boundaries of a cluster are, as a result of the shape of the vessel contour, expanded such that they lie at the end of nearby concave curve sections of the contour, if said sections can be identified.

Figure 10:
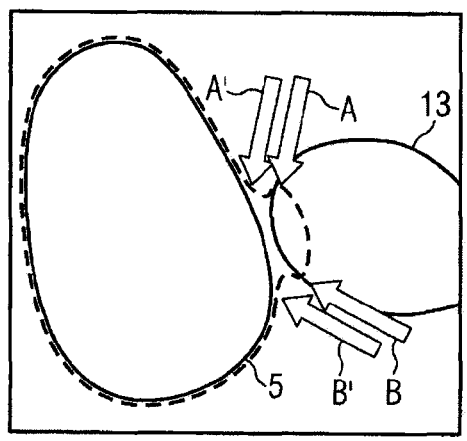
FIG. 10 shows a schematic illustration for explaining the removal of outliers or not sufficiently fitted contour points and/or contour sections in the second initial contour, FIG. 11 corresponds to FIG. 6 and is only imaged again for making FIG. 12 easier to understand, FIG. 12 corresponds to FIG. 7 in the case of the lower graph and this part is only imaged again for making the upper graph of FIG. 12 easier to understand. The upper graph shows the correlation of the image values determined in the lower graph of FIG. 12 with the learnt edge model (also c.f.
Figure 13:
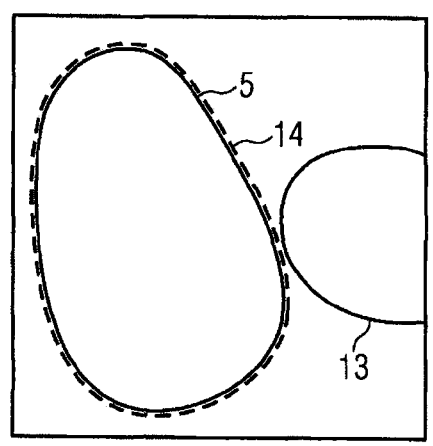
FIG. 13 is a schematic illustration of a 2D contour 14 fitted sufficiently well to the vessel contour 5 and FIG. 14 is a schematic illustration of the improvement of approximations of the 2D contours by iterative refinement or addition of contour points (in this case, four and eight contour points).

FIG. 10 shows that an outlier is identified in a section A->B because the second initial 2D contour lies in a very bright region (vessel lumen of the adjacent vessel 13) after a predetermined number of iterations. Subsequently, the length of the section A'->B' of the second initial 2D contour to be adjusted is determined by identifying regions with a concave curvature. The initial point and end point of the section to be corrected are then corrected to the initial and end points of these curves.

Figure 11:
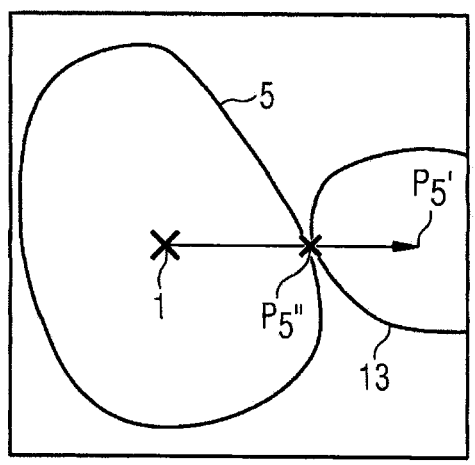
Figure 12:
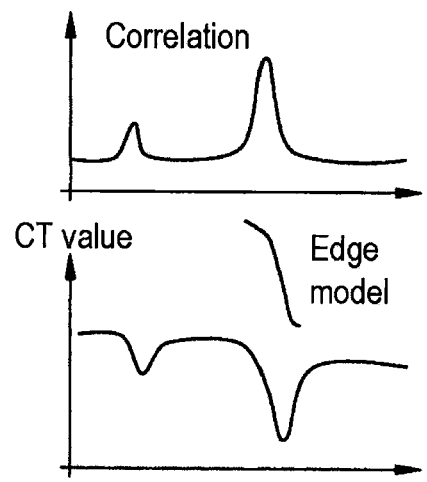

Outliers are removed in a further step 106bc. To this end, a position of maximum correlation of the learnt edge model along search rays is determined for the contour points $P_i'$ or $P_i''$. In the process, the second 2D contour is fitted to these maxima in this region using an active 2D contour model. The lower graph of FIG. 12 shows the CT value profile for the ray illustrated in FIG. 11 from the central line 1 to point $P_5'$. The upper graph of FIG. 12 plots the corresponding profile of the correlation value between CT value profile and learnt edge model. The corrected contour point $P_5''$ is determined at the point with the best correlation.

Figure 14:
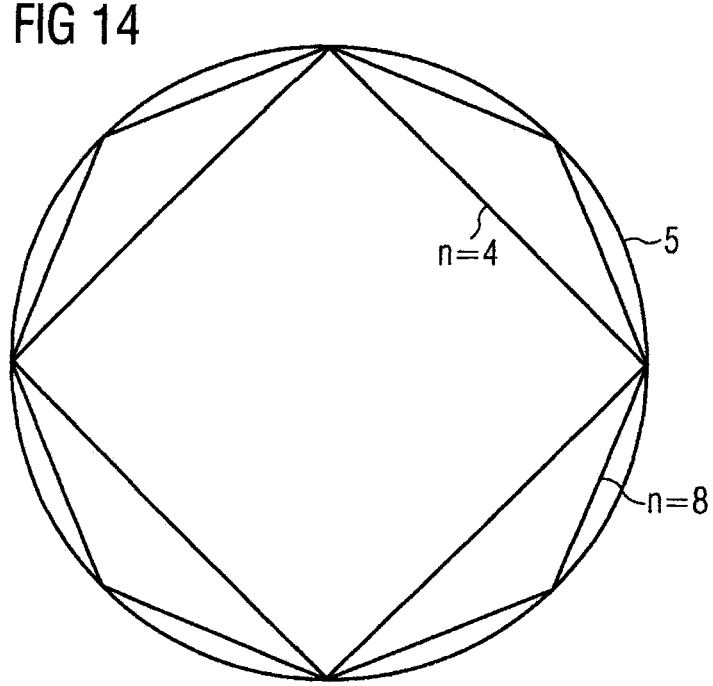

The steps 106a and 106b, including the sub-steps, are performed iteratively with an increasing number of contour points until the required accuracy was achieved. To this end, FIG. 14 schematically shows the effect of an increase in the number of determined contour points $P_i$ on the accuracy of the fit of the 2D contour to the vessel structure.

In order to calculate a profile curve, 2D contours have to be determined for a large number of central line points and the area thereof has to be measured. The specified method has to be run for every 2D contour and so the calculation time per 2D contour is in the region of a few microseconds on modern PCs and it adds up to up to 30 seconds for up to 1000 central line points. So that an approximate curve profile is displayed to the user as quickly as possible, a rough approximate profile curve profile is firstly displayed, which becomes more and more refined.

To this end, the cross-sectional areas at the two end points are calculated first and, assuming a linear profile, they are connected in the graph by a straight line. Subsequently, the interval is halved and the cross-sectional area is determined in the middle. The graph can now be complemented by this new measurement. The linearly approximated intervals are now treated in a corresponding fashion, with the cross-sectional areas in each case subsequently being determined in the middle of said intervals. This method of interval nesting is carried out until a sufficient quality has been achieved or a predetermined maximum calculation time is reached.

The described example embodiment affords the possibility of also finding 2D contours in vessel sections in which thresholds are not overshot or undershot in a precise fashion, but which allow a continuation of the contour profile to be recognized on the basis of a visible, vessel-contour-typical decrease or increase in brightness. In the process, the 2D contour refined in two dimensions is first of all calculated in 3-dimensional space and is used as an initialization for the 2-dimensional contour by a slice in the image plane. An active contour model (ACM) recognizes at which points the second 2D contour is not yet on the contour of the vessel. In such contour sections, the 2D contour is fitted to the vessel contour using an autonomously learning 2D contour model. In the process, a universal method is used which does not build on specific image features (edges, grayscale values, texture, etc.) but is trained on the basis of already correctly fitted contour points.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a 2D contour of a vessel structure imaged in 3D image data for a first slice plane of the vessel structure, wherein the 3D image data is generated using a medical imaging system and has a multiplicity of image voxels which are all assigned a respective image value, the method comprising:

providing the 3D image data;

determining, by a processor, a multiplicity of first initial 2D contours of the vessel structure based on a first threshold, wherein the first initial 2D contours in the 3D image data are determined for slice planes of the vessel structure, the planes being arranged orthogonally with respect to a central line of the vessel structure and spaced apart from one another along the central line;

adjusting, by the processor, the first initial 2D contours such that an overlapping of any one of the first initial 2D contours with an adjacent vessel is eliminated, the adjusting being made based on a second threshold;

determining, by the processor, a first initial 3D contour from the determined first initial 2D contours;

determining, by the processor, a smoothed second 3D contour by applying an active 3D contour model to the first initial 3D contour;

determining, by the processor, a second initial 2D contour as a slice through the smoothed second 3D contour including the first slice plane; and determining, by the processor, the 2D contour by iteratively fitting the second initial 2D contour to the vessel structure imaged in the 3D image data which results for the first slice plane.

2. The method as claimed in claim 1, wherein a number n of contour points $P_i$ with $i=1, \ldots, n$ is determined for each slice plane in the determining of the multiplicity of first initial 2D contours by evaluating the 3D image data, wherein each of the first initial 2D contours results in a closed continuous line which connects the contour points determined for the respective slice plane.

3. The method as claimed in claim 2, wherein the closed continuous line is a polygon.

4. The method as claimed in claim 3, wherein image values of image voxels, which respectively lie on one of n rays emanating radially from the central line are evaluated in order to determine the n contour points per slice plane in the image data, and wherein
- the n rays lie in the slice plane and have an angular distance from one another,
- the evaluation of the image values starting at the central line continues radially outward along the rays, and
- a contour point is detected on one of the n rays if the image value of an image voxel satisfies a threshold or gradient criterion.

5. The method as claimed in claim 2, wherein image values of image voxels, which respectively lie on one of n rays emanating radially from the central line are evaluated in order to determine the n contour points per slice plane in the image data, and wherein
- the n rays lie in the slice plane and have an angular distance from one another,
- the evaluation of the image values starting at the central line continues radially outward along the rays, and
- a contour point is detected on one of the n rays if the image value of an image voxel satisfies a threshold or gradient criterion.

6. The method as claimed in claim 5, wherein the image values along the n rays are each only evaluated up to a maximum radius and a contour point is fixed on the respective ray at the maximum radius if no contour point is detected.

7. The method as claimed in claim 2, wherein individual or a number of steps of the method are executed repeatedly for, in each case, an increased number n of contour points.

8. The method as claimed in claim 1, wherein an active 2D contour model is applied to determine at least one of the first initial 2D contours in the determining of the multiplicity of first initial 2D contours and the 2D contour in the determining of the 2D contour.

9. The method as claimed in claim 8, wherein the active 2D contour model is based on thresholds.

10. The method as claimed in claim 1, wherein the medical imaging system is at least one of a CT, CTA, MRI, PET, SPECT and a duplex sonography system.

11. The method as claimed in claim 1, wherein the 3D image data are 3D CTA image data.

12. The method as claimed in claim 1, wherein the first initial 3D contour is determined using a triangulation method.

13. The method as claimed in claim 1, wherein an evaluation method based on at least one of thresholds and gradients is applied to determine at least one of the first initial 2D contours in the determining of the multiplicity of first initial 2D contours and the 2D contour in the determining of the 2D contour.

14. The method as claimed in claim 1, wherein the slice planes are arranged at a constant spacing along the central line.

15. The method as claimed in claim 1, wherein the first slice plane is arranged orthogonally with respect to the central line.

16. The method as claimed in claim 1, wherein the first slice plane is one of the slice planes of the determining of the multiplicity of the first initial 2D contours.

17. The method as claimed in claim 1, wherein the determining of the 2D contour comprises:
- fitting the second initial 2D contour using a threshold-based active 2D contour model,
- determining at least one of contour points and contour sections which are not fitted in a satisfactory fashion in the fitting of the second initial 2D contour, and
- applying an active 2D contour model based on an unmonitored learning edge model to at least one of the contour points and contour sections determined, wherein training data for the unmonitored learning 2D contour model is determined from at least one of already satisfactorily fitted contour points and contour sections from the fitting of the second initial 2D contour.

18. A non-transitory computer readable medium including a computer-readable program product, the computer readable program product comprising instructions, which when executed on a computer device, causing the computer device to perform functions for determining a 2D contour of a vessel structure imaged in 3D image data for a first slice plane of the vessel structure, wherein the 3D image data is generated using a medical imaging system and has a multiplicity of image voxels which are all assigned a respective image value, the functions including:
- providing 3D the image data;
- determining a multiplicity of first initial 2D contours of the vessel structure based on a first threshold, wherein the first initial 2D contours in the 3D image data are determined for slice planes of the vessel structure, the planes being arranged orthogonally with respect to a central line of the vessel structure and spaced apart from one another along the central line;
- adjusting, by the processor, the first initial 2D contours such that an overlapping of any one of the first initial 2D contours with an adjacent vessel is eliminated, the adjusting being made based on a second threshold;
- determining a first initial 3D contour from the determined first initial 2D contours;
- determining a smoothed second 3D contour by applying an active 3D contour model to the first initial 3D contour;
- determining a second initial 2D contour as a slice through the smoothed second 3D contour including the first slice plane; and
- determining the 2D contour by iteratively fitting the second initial 2D contour to the vessel structure imaged in the 3D image data which results for the first slice plane.

* * * * *